(12) United States Patent
Connelly et al.

(10) Patent No.: US 6,488,704 B1
(45) Date of Patent: Dec. 3, 2002

(54) IMPLANTABLE PARTICLE MEASURING APPARATUS

(75) Inventors: Patrick R. Connelly, Rochester, NY (US); Thomas H. Foster, Rochester, NY (US)

(73) Assignee: Biomed Solutions, LLC, West Henrietta, NY (US)

( * ) Notice: Subject to any disclaimer, the term of this patent is extended or adjusted under 35 U.S.C. 154(b) by 39 days.

(21) Appl. No.: 09/850,250

(22) Filed: May 7, 2001

(51) Int. Cl.⁷ .................................. A61F 2/06

(52) U.S. Cl. ...................... 623/1.15; 604/265

(58) Field of Search ................... 600/309–310, 600/342, 407, 473, 476; 623/1.1, 1.11–1.19, 1.2, 1.21–1.22; 606/108, 191–200; 604/265

(56) References Cited

U.S. PATENT DOCUMENTS

| | | | | |
|---|---|---|---|---|
| 5,865,814 A | * | 2/1999 | Tuch | 424/426 |
| 5,964,751 A | * | 10/1999 | Amplatz et al. | 606/15 |
| 6,119,031 A | * | 9/2000 | Crowley | 600/310 |
| 6,124,523 A | * | 9/2000 | Banas et al. | 606/191 |
| 6,200,307 B1 | * | 3/2001 | Kasinkas et al. | 606/15 |

* cited by examiner

Primary Examiner—Robert M. Fetsuga
Assistant Examiner—Amanda Flynn
(74) Attorney, Agent, or Firm—Greenwald & Basch LLP; Howard J. Greenwald (57) ABSTRACT

An implantable stent which contains a tube, several optical emitters located on the inner surface of the tube, and several optical photodetectors located on the inner surface of the tube. The optical emitters radiate energy with a wavelength of from about 30 nanometers to about 30 millimeters, and the optical photodectors receive energy with a wavelength of from about 30 nanometers to about 30 millimeters.

43 Claims, 9 Drawing Sheets

IMPLANTABLE PARTICLE MEASURING APPARATUS

FIELD OF THE INVENTION

An implantable particle measuring apparatus which can be used for diagnostic purposes for individuals who are susceptible to specific cancers; the device can also be used as a health monitoring system for routine analysis of specific cellular factors in bodily fluid.

BACKGROUND OF THE INVENTION

Flow cytometers are well known to the art. Thus, for example, U.S. Pat. No. 6,097,485 discloses a miniature flow cytometer adapted to measure laser-induced fluorescence.

The flow cyomteter of U.S. Pat. No. 6,097,485 is not implantable, it is not capable of utilizing and analyzing the living organism's unmodified fluids, and it is not capable of communicating with other devices inside or outside of an organism.

It is an object of this invention to provide an implantable particle analzyer which is capable of analyzing endogenous body fluid, and which contains telemetric means for communicating with controllers and/or programmers external to the body.

SUMMARY OF THE INVENTION

In accordance with this invention, there is provided an implantable particle size analyzer which comprises a flexible tube comprising an inner surface and an outer surface, a multiplicity of monolithic laser photodetectors disposed on the inside surface of the tube, a means of optically connecting said photodetectors to each other, a monolithic integrated circuit chip for the integration and control of received signals, and means for operatively connecting said chip to said photodetectors.

BRIEF DESCRIPTION OF THE DRAWINGS

The invention will be described by reference to the specification and the enclosed drawings, in which like numerals refer to like elements, and in which.

DESCRIPTION OF THE PREFERRED EMBODIMENTS

Flow cytometry (FC) is used to detect variations in cell types and/or particles by use of fluorescent labeling and endogenous cellular optical properties. Originally flow cytometric systems were used solely to rapidly count cells. The cells were traditionally isolated from tissue or blood and labeled with fluorescent markers or antibodies conjugated with fluorescent tags. A variety of cell types have been analyzed using these methods. Cell volume and type could also be characterized by the intensity and frequency component of transmitted light. Following isolation, cells were then fed through a flow chamber of specified dimensions.

Optical FC systems are based on either the detection of intrinsic scattering properties of cells (which include the cellular membrane structure, organelle concentration and structure, cytoplasmic structure, and DNA/chromatin structure) and/or of detection of emitted light from fluorescently labeled cells. The cells are usually labeled with fluorescent conjugated antibodies to cell surface receptors or cytoplasmic proteins. A source for the emission of a specified frequency of energy (i.e., a light source) is directed toward the stream of flowing cells through a narrow flow cell. It is possible to detect with a photomultiplier tube array the scattering of light through the cell ("forward light scattering"), the scattered light which is reflected orthogonal to the direction of the flow ("side light scattering"), and the fluorescence emission from fluorescendy conjugated antibodies to a variety of factors within and on the cell surface.

In the process of the present invention, a particle analyzer is provided that is also capable of being used as a stent. As is known to those skilled in the art, and as is disclosed in U.S. Pat. No. 6,190,393 (the entire disclosure of which is hereby incorporated herein by reference), a stent is a flexible cylinder or scaffold made of metal or polymers; and it may be permanently implanted into a blood vessel following an angioplasty procedure. The stent tends to hold the lumen open longer, to reinforce the vessel wall, and to improve blood flow.

To improve efficiency and reduce time required for the vascular procedure, it is desirable to combine these angioplasty and stent deployments. This combined procedure may be referred to as "primary stenting" or "direct stenting."

During a primary stenting procedure, an initial angioplasty is not performed. Rather, a modified stent delivery system is used to cross or traverse a lesion or stenosis, and to expand the desired site in a fashion similar to angioplasty and deploy a stent. In this direct stenting procedure, the stent delivery system is first advanced within the patient's body until the stent is located within the desired site where the lesion or stenosis is present.

The particle analyzer of this invention may be inserted into a living organism in the same manner as is commonly done with primary stenting. One preferred embodiment of such particle analyzer is illustrated in FIG. 1.

Figure 1:
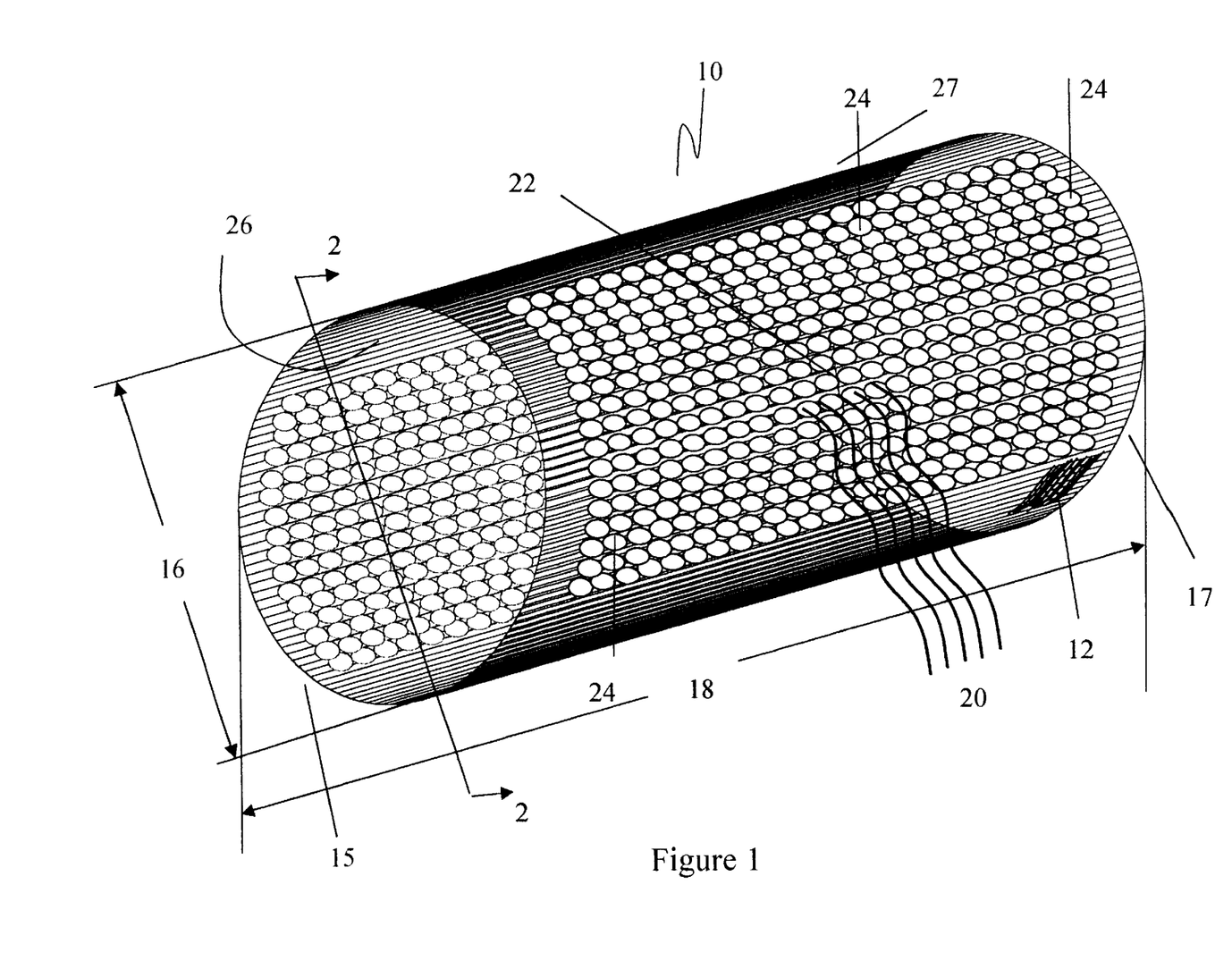
FIG. 1 is a perspective view of one preferred particle analyzer of the invention.

FIG. 1 is a perspective view of one preferred particle analyzer 10 of this invention. Referring to FIG. 1, it will be seen that particle analyzer 10 is comprised of a casing (not shown in FIG. 1) and an interior surface 26.

In the preferred embodiment depicted in FIG. 1, particle analyzer 10 has an external diameter 16 of from 100 micrometers to about 3 millimeters and, preferably, from about 250 to about 700 microns. Additionally, particle analyzer 10 has a length 18 of from about 500 microns to about 5 centimeters and, preferably, from about 1 centimeter to about 3 centimeter.

The particle analyzer 10 is flexible and deformable. It has relatively thin walls. Thus, e.g., the difference between its internal diameter and its external diameter is generally from about 50 microns to about 3 millimeters and, more preferably, from about 50 microns to about 500 microns.

When radiation 20 impacts the outer surface 22 particle analyzer 10, less than 0.5 percent of such radiation is transmitted through the particle analyzer 10, and less than about 0.5 percent of such light rays are absorbed. As will be apparent, this property of optical impermeability insures that the sensing function of particle analyzer 10 is not affected by radiation emanating from outside of such particle analyzer 10.

In order to effect such optical impermeability, it is preferred that the casing 12 be made from an optically impermeable material which, additionally, is biocompatible with the living organism. Thus, e.g., casing 12 may be made, e.g., from a polymer composite material. One may use, e.g., any of the biocompatible optical shields with the required transmittance and absorbance properties.

In one embodiment, the casing 12 is comprised of a flexible biocompatible material with the ability to inhibit the transmission of optical energies into the lumen of the stent. Thus, for example, one may use one or more of the biocompatible materials disclosed in U.S. Pat. No. 6,124,523. This patent discloses an encapsulated stent including a stent or structural support layer sandwiched between two biocompatible flexible layers. One preferred embodiment has a stent cover which includes a tubular shaped stent that is concentrically retained between two tubular shaped grafts of expanded polytetrafluoroethylene. Another preferred embodiment has a stent graft which includes at least one stent sandwiched between the ends of two tubular shaped grafts wherein at least a portion of the grafts are unsupported by the stent.

In one embodiment, casing 12 is comprised of or consists essentially of polyetrafluorethylene. In additional embodiments, other biocompatible fluoroplastic materials may be used for casing 12.

Referring again to FIG. 1, the particle analyzer 10 is comprised of means for delivering one or more anticoagulants and/or proteinases to bodily fluid flowing within the particle analyzer 10 at a controlled delivery rate. In one preferred embodiment, the process described in U.S. Pat. No. 5,865,814 (the entire disclosure of which is hereby incorporated by reference into this specification) is used to deliver anticoagulant and/or proteinase at a specified rate. This patent discloses a medical device for use in contact with circulating blood comprising: (a) a medical device having a blood-contacting surface; (b) a first coating layer on the blood-contacting surface consisting essentially of water soluble heparin; and (c) a second coating layer comprising a porous polymer overlaying the first coating layer such that heparin is elutable from the medical device through the second coating layer.

Referring again to FIG. 1, and in the preferred embodiment depicted therein, it will be seen that a particle analyzer 10 is comprised of a multiplicity of light emitting systems 24. In the preferred embodiment depicted in FIG. 1, these light emitting systems 24 are preferably each equipped with an emitter (not shown in FIG. 1) and a photodetector (not shown in FIG. 1) in a monolithic configuration.

Referring again to FIG. 1, it will be seen that the light emitting systems 24 are present on the inside surface 26 of the particle analyzer 10 at a density of from about 3 to about 10 such systems 24 per square millimeter of surface 26 and, more preferably, at a density of from about 4 to about 7 such systems 24 per square millimeter of surface 26.

In one preferred embodiment, the light emitting systems 24 are uniformly distributed on the inside surface 26 of the particle analyzer 14. In another embodiment, illustrated in FIG. 1, the light emitting systems are recessed from each end edge 15 and 17 by a distance of at least about 2 millimeters to minimize the opportunity for spurious radiation entering the ends of particle analyzer 10 and causing false readings.

Each light emitting system 24 is preferably comprised of means for both emitting light and sensing light. The light emitter (not shown in FIG. 1) is preferably adapted to emit light across the electromagnetic spectrum, from a wavelength of from about 30 nanometers to about 30 millimeters (far infrared), and more preferably a wavelength of from about 350 (ultraviolet and argon lasers) to about 900 nanometers.

In general, the light emitting system may emit any electromagnetic radiation. It is preferred, however, that at least one of the forms of electromagnetic radiation emitted is optical radiation.

In one embodiment, the optical spectra emitted by any particular light emitting system 24 may differ from the optical spectra emitted by another such light emitting system 24. As will be discussed elsewhere in this specification, periodic arrays of such light emitting systems 24 with differing optical outputs may be used.

In addition to containing means for emitting light, the light emitting assemblies 24 also preferably contain means for detecting light of specified optical properties, as will be discussed in more detail elsewhere in this specification.

Figure 2:
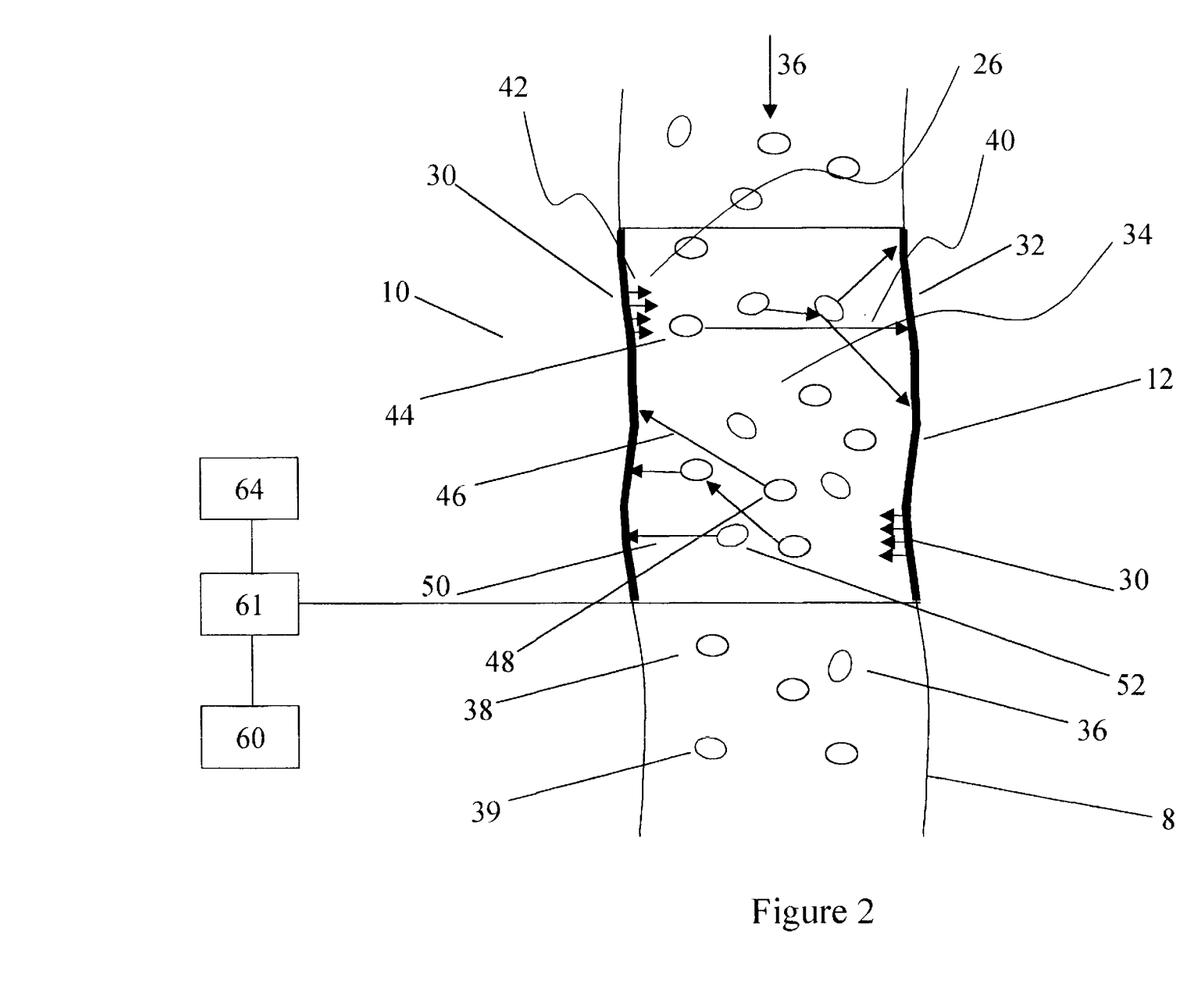
FIG. 2 is a sectional view of the particle analyzer of FIG. 1 inserted within a living organism.

FIG. 2 is a partial sectional view of the particle analyzer 10, taken through lines 2—2 of FIG. 1. For the purposes of illustration, the various components and cells depicted in FIG. 2 are not drawn to scale.

Referring to FIG. 2, it will be seen that casing/flexible substrate 12 has disposed on its inside surface 26 light emitting devices 30 and light sensing devices 32. Although, in the embodiment depicted in FIG. 2, devices 30 and 32 are shown separately disposed within casing 12 for the sake of simplicity of representation, it should be understood that the devices 30 and 32 are preferably part of one monolithic construct 24. Reference may be had, e.g., to FIG. 4.

In one embodiment, the preferred emitter 30 is a "vertical cavity surface emitting laser" (VCSEL). A VCSEL emits light perpendicular to the wafer as the name implies. An advantage of VCSELs is that they are capable of being modulated at high speeds with much lower electrical power than in-plane lasers. In addition, the geometry of VCSELs makes them particularly suitable for making two-dimensional arrays, and for on-wafer testing. These characteristics can reduce the cost of packaging (which dominates the cost of manufacturing) and costs of the driver circuitry required.

Referring again to FIG. 2, and in the embodiment depicted therein, a bodily fluid 34 is flowing in the direction of arrow 36. In one embodiment, the bodily fluid 34 is blood, and it is caused to flow by the action of a heart.

In another embodiment, the bodily fluid may be a non-hematologic fluid such as, e.g., lymph, urine, cerebrospinal fluid, and the like.

In one embodiment, the bodily fluid 34 is comprised of plasma. In another embodiment, the bodily fluid 34 is comprised of red blood cells 36, and/or leukocytes 38, and/or neutrophils 39, and/or other cells or cellular material. Each of these components will have a different optical response to a specified optical input Thus, referring again to FIG. 2, the cells preferably have either endogenous optical properties, and/or they are labeled to provide optical properties. Thus, e.g., the cells may be labeled with fluorescently-conjugated antibodies. Thus, e.g., in one embodiment the device 10 will utilize either injected fluorescent contrast or emitted light energies intrinsic to specific cells themselves. As is known to those skilled in the art, antibodies may be conjugated with polymeric dies with fluorescent emission moieties such as aminostyryl pyridinium (see, e.g., U.S. Pat. No. 5,994,143, the entire disclosure of which is hereby incorporated by reference into this specification).

As is apparent, and in one preferred embodiment, the function of flow cytometry system 10 is to determine which, if any, of four antigens are carried by blood cells, including cell CEL. To this end, respective antibodies for the antigens are derivatized with respective fluorochromes allophycocyanin (APC), peridinin chlorophyl protein (PerCP), fluorescein isothiocyanate (FITC), and R-phycoerythrin (RPE). Reference may be had, e.g., to U.S. Pat. No. 5,682,038 for "Fluorescent-particle analyzer with timing alignment for analog pulse subtraction of fluorescent pulses arising from different excitation locations," the entire disclosure of which is hereby incorporated by reference into this specification.

By way of further illustration, U.S. Pat. No. 5,994, 143 ("Polymeric fluorophores enhanced by moieties providing a hydrophobic and conformationally restrictive microenvironment") discloses another process for fluorescent antibody conjugation; the entire disclosure of this United States patent is hereby incorporated by reference into this specification. In this patent, it is disclosed that the first of two closely positioned fluorophores may be excited by light of a given wavelength. Then, instead of emitting light of a longer wavelength, the excited fluorophore transfers energy to the second fluorophore. That transferred energy excites the second fluorophore, which then emits light of an even longer wavelength than would have been emitted by the first fluorophore. An example of such an energy transfer arrangement involves plycobiliprotein-cyanine dye conjugates. Subjecting these conjugates to an about 488 nm laser light excites the phycobiliprotein. The phycobiliprotein will then, without itself irradiating, transfer energy to the cyanine fluorophore at the excitation wavelength of the cyanine, which is coincident with the emission wavelength of the phycobiliprotein, about 580 nm. Consequently, the cyanine fluorophore is thereby excited and subsequently emits light of its emission wavelength of about 680 nm. This type of energy transfer system in often referred to as a "tandem energy transfer system."

In one embodiment, not shown, fluorescent dyes are injected upstream of the device 10, preferably into a venous blood supply. The dyes may be injected in a manner similar to that used to inject contrast agents for medical ultrasound techniques. See, e.g., U.S. Pat. No. 6,177,062 ("Agents and methods for enhancing contrast in ultrasound imaging"), the entire disclosure of each of which is hereby incorporated by reference into this specification. The fluorescent dyes preferably are not toxic to the living body and care must be taken in preparation of the fluorescent dyes. The combination of different wavelength fluorochromes conjugated to antibodies to different cells along with the endogenous optical properties of the cells will provide a complex multiparameter data set where differing signals from different cells will be discernable.

In one embodiment, depicted in FIG. 2, the device 10 detects the intrinsic scattering properties of cells (which are influenced by the cellular membrane structure, organelle concentration and structure, cytoplasmic structure, and DNA/chromatin structure) and/or emitted light from fluorescendy labeled cells.

Referring again to FIG. 2, the device 10 is contacting the bodily fluid 36 with a multiplicity of different optical radiations 42, and a multiplicity of different phenomena are occurring which are sensed by the device 10.

Thus, by way of illustration, emitter 30 emits radiation 42 that contacts cell 44, which is transmitted directly through the cell 44, and which emerges as radiation 40. The emitted radiation 40 is sensed by sensor 32. As will be apparent to those skilled in the art, this process is often referred to as "forward light scattering."

In addition to detecting forward light scattering, the device 10 is also capable of detecting the scattered light that is reflected orthogonal to the direction of the flow ("side light scattering").

Reference may be had to radiation 46 scattered by cell 48.

Furthermore, the device 10 may also detect the fluorescence emission from fluorescently conjugated antibodies to a variety of factors within and on the cell surface. Reference may be had, e.g., to radiation 50 emitted by cell 52.

In one embodiment, and referring again to FIG. 2, the device 10 is comprised of a telemctric device 60, such as a transceiver 60, which may be disposed within or without a person's body. One may use any of the implantable telemetry devices known to those skilled in the art. Reference may be had, e.g., to an article by Z. Hamici entitled "A high-efficiency power and data transmission system for biomedical implanted electronic devices," published in Measurement Science Technology 7 (1996), at pages 192–201. The authors of this article described a new system energizing an implanted micro-telemeter that transmits internal digital data to a remote receiver.

By way of further illustration, one may use the transceiver disclosed in U.S. Pat. No. 5,972,029 ("Remotely operable stent"). In the process of this patent, the diameter of the stent is varied mechanically using strut mechanisms that are operatively connected to the transceiver. The transceiver of this patent utilizes electromagnetic radiation in the infrared region.

Similarly, one may use the telemetry system disclosed in U.S. Pat. No. 5,843,139 ("adaptive, performance-optimizing communication system for communicating with an implanted medical device").

Regardless of the telemetry system used, it is also understood that the telemetric device may not only use radio frequency energy for telemetric functions but also may utilize acoustic energy. Reference may be had, e.g., to U.S. Pat. No. 6,170,488 ("Acoustic-based remotely interrogated diagnostic implant device and system"), the entire disclosure of which is hereby incorporated by reference into this specification.

Referring again to FIG. 2, it will be apparent that, for any particular bodily fluid sample at any particular point in time, there will be a multiplicity of radiations emitted by the device 10, and a multiplicity of radiations sensed by the device 10. Thus, the device 10 is capable of detecting a myriad of different conditions and/or phenomena. The data so detected will be processed by a controller 64, which is preferably operatively connected to both telemetry device 60, emitters 32, and a waveguide layer (see, e.g., layer 72 in FIGS. 4*a* and 4*b*).

Referring again to FIG. 2, the controller 64 and/or the telemetry device 60 are powered by power supply 61. One may use conventional power supplies. Thus, by way of illustration, one may use a lithium-iodine battery, and/or a battery that is chemically equivalent thereto. The battery used may, e.g., have an anode of lithium or carbon and a cathode of iodine, carbon monofluoride, or of silver vanadium oxide, and the like.

By way of further illustration, one may use one or more of the batteries disclosed in U.S Pat. No. 5,658,688 ("lithium-silver oxide battery and lithium-mercuric oxide battery"), U.S. Pat. No. 4,117,212 ("lithium-iodine battery"), and the like. The entire disclosure of each of these United States patents is hereby incorporated by reference into this specification.

Figure 7:
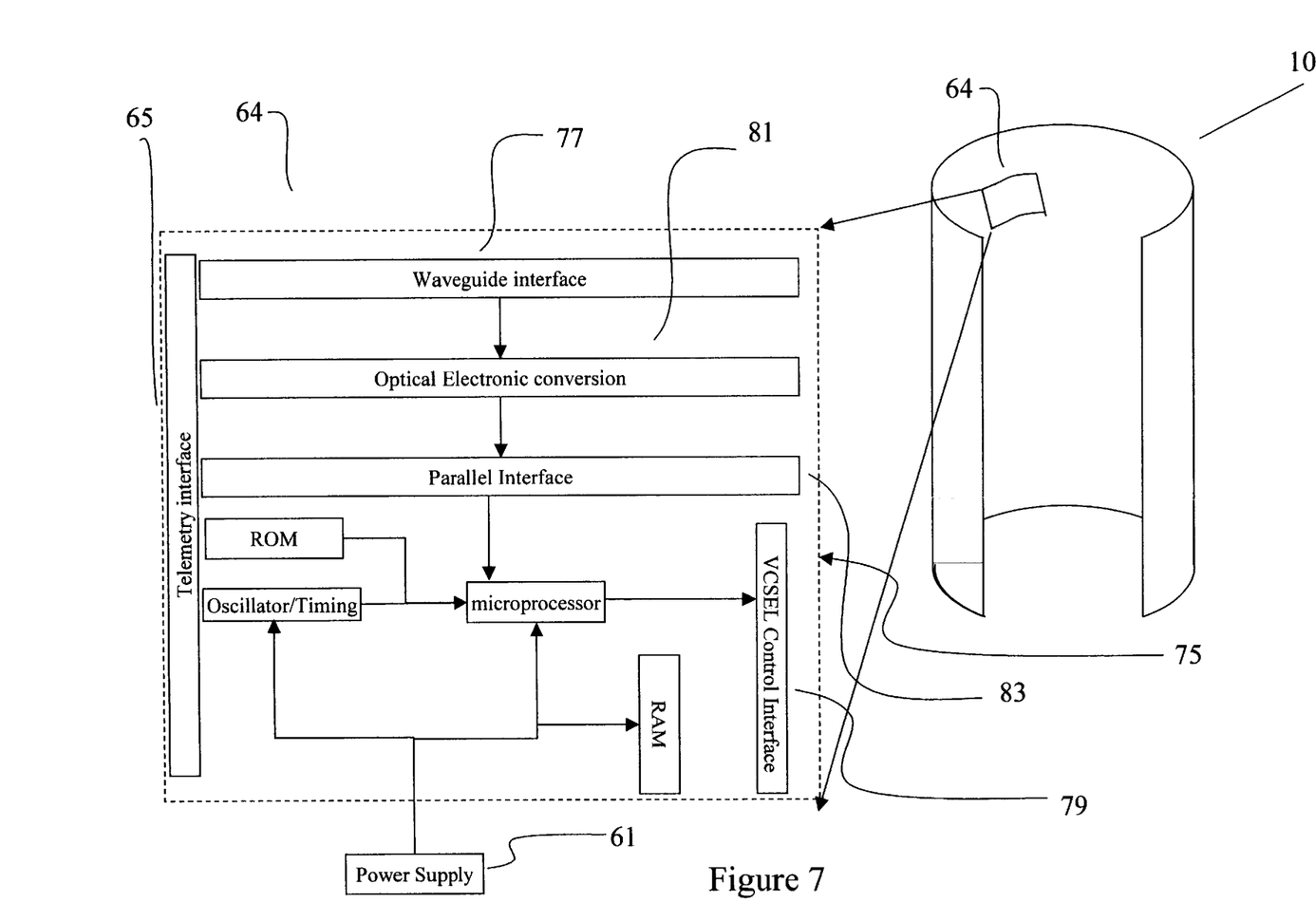
FIG. 7 is a partial exploded view of the particle analyzer of FIG. 1 illustrating a preferred controller/signal processor used therein.

In one embodiment, illustrated in FIG. 7, the power supply 61 is incorporated into the housing of the controller/processor 64.

The telemetry device 60 and the controller 64 may be used with the other components of applicant's analyzer 10 to evaluate, process, store, and utilize the information detected from the bodily fluid.

Because many different types of data are analyzed for any particular bodily fluid sample, the device 10 is capable of accurately analyzing many different conditions.

By way of illustration, and by reference to the process depicted in U.S. Pat. No. 6,014,904, one may analyze the bodily fluid and its constituents. This patent discloses a method for automatically classifying multi-parameter data into cluster groups for the purpose of defining different populations of particles in a sample by automatically defining a position of at least one variable position, geometric boundary surface on a two-dimensional scatter plot so as to enclose a group of the displayed particles in a data cluster, with the boundary surface having a polygonal shape defined by a plurality of vertices about at least one cell cluster created by building at least one histogram from cross sections of the two-dimensional gate. The method is particularly useful in the field of cellular analysis using, for example, flow cytometers wherein multi-parameter data is recorded for each cell that passes through an illumination and sensing region. The entire disclosure of this United States patent is hereby incorporated by reference into this specification.

By way of further illustration, multiparameter data sets acquired from the various photo-detectors may be processed with algorithms such as that taught in U.S. Pat. No. 5,627,040. The entire disclosure of this United States patent is hereby incorporated by reference into this specification.

By way of yet further illustration, one may use the technology of one or more of the patents described below for analyses of the many different signals to be received by the array of photodetectors.

U.S. Pat. No. 5,880,474 ("Multi-illumination-source flow particle analyzer with inter-location emissions crosstalk cancellation") describes a process in which the photodetector output signals are processed by analog signal processor, which includes a crosstalk cancellation integrated circuit, a transit delay circuit, an amplifier bank, a pulse processor, a peak holder, and an analog-to-digital converter (ADC).

U.S. Pat. No. 5,602,647, for "Apparatus and method for optically measuring concentrations of components," discloses an apparatus and method for optically measuring concentrations of components allow enhancement in measurement accuracy of concentration. In the process of this patent, and in one embodiment of the process of applicant's patent, an array of photodetectors is arranged in parallel to the surface of a multiplicity of cells, so that it can detect intensity of rays of transmitted light and/or fluorescent emissions that have traveled over different optical path lengths at positions of an equal distance from the cell. The arithmetic unit, receiving a signal from the individual photodetectors, calculates concentrations of components in the sample based on optimum optical path lengths for different wavelengths and values of transmitted light at positions of the optimum optical path lengths, and further outputs calculation results. The entire disclosure of this patent is hereby incorporated by reference into this specification.

By way of further illustration, in U.S. Pat. No. 5,682,038, for "Fluorescent-particle analyzer with timing alignment for analog pulse subtraction of fluorescent pulses arising from different excitation locations," additional methods are described to alleviate crosstalk it will be apparent that, with regard to applicants' process, the number of distinguishable fluorochromes can be increased by using more than one excitation wavelength. This approach takes advantage of the fact that fluorochromes differ not only in their emissions spectra, but also in their excitation spectra. In an ideal case, two fluorochromes with non-overlapping excitation spectra could be distinguished even where the emissions spectra were identical. The distinction could be achieved by illuminating the fluorochromes at different times with two lasers, each selected to excite only a respective one of the fluorochromes. The resulting emissions would appear as two distinct pulses in the output of a single photodetector.

The U.S. Pat. No. 5,682,538 patent discloses an approach that is implemented in the context of a flow cytometry system by illuminating different locations along a flow tube with different laser wavelengths, each of which preferentially excites a respective fluorochrome. As is disclosed in such patent, tagged cells are made to flow serially past the two locations. When a cell is at the first location, a photodetector pulse corresponds to the first fluorochrome; when later the cell is at a second location, a photodetector pulse corresponds to the second fluorochrome. The pulses are routed and at least minimally processed in the analog domain; they are then converted to digital data that can then be manipulated in the digital domain to provide the desired information about the cells.

As is disclosed in U.S. Pat. No. 5,682,538, in such a flow cytometry system, each pulse generated corresponds predominantly to a respective fluorochrome. Because of overlapping emissions and excitation spectra, each pulse can include contributions, i.e., "crosstalk", from other fluorochromes. Two types of crosstalk can be distinguished: "intrabeam" crosstalk results from overlap in the emissions spectra of fluorochromes excited by a common laser beam; "interbeam" crosstalk results from the overlap in the excitation spectra of fluorochromes excited by different laser beams. There are optical techniques for reducing both types of crosstalk, but they are incomplete. Accordingly, post-detection correction of crosstalk is required.

By way of further illustration, U.S. Pat. No. 5,632,538 discloses that the mathematics of crosstalk reduction is well understood. In general, crosstalk can be removed from a measurement primarily corresponding to one fluorochrome by subtracting a crosstalk term that is a function of measurements primarily corresponding to the other fluorochromes. More specifically, the crosstalk term can be a sum of product terms; each product term is a fluorochrome measurement multiplied by a coefficient. The coefficients can be determined empirically during a calibration run.

Figure 3:
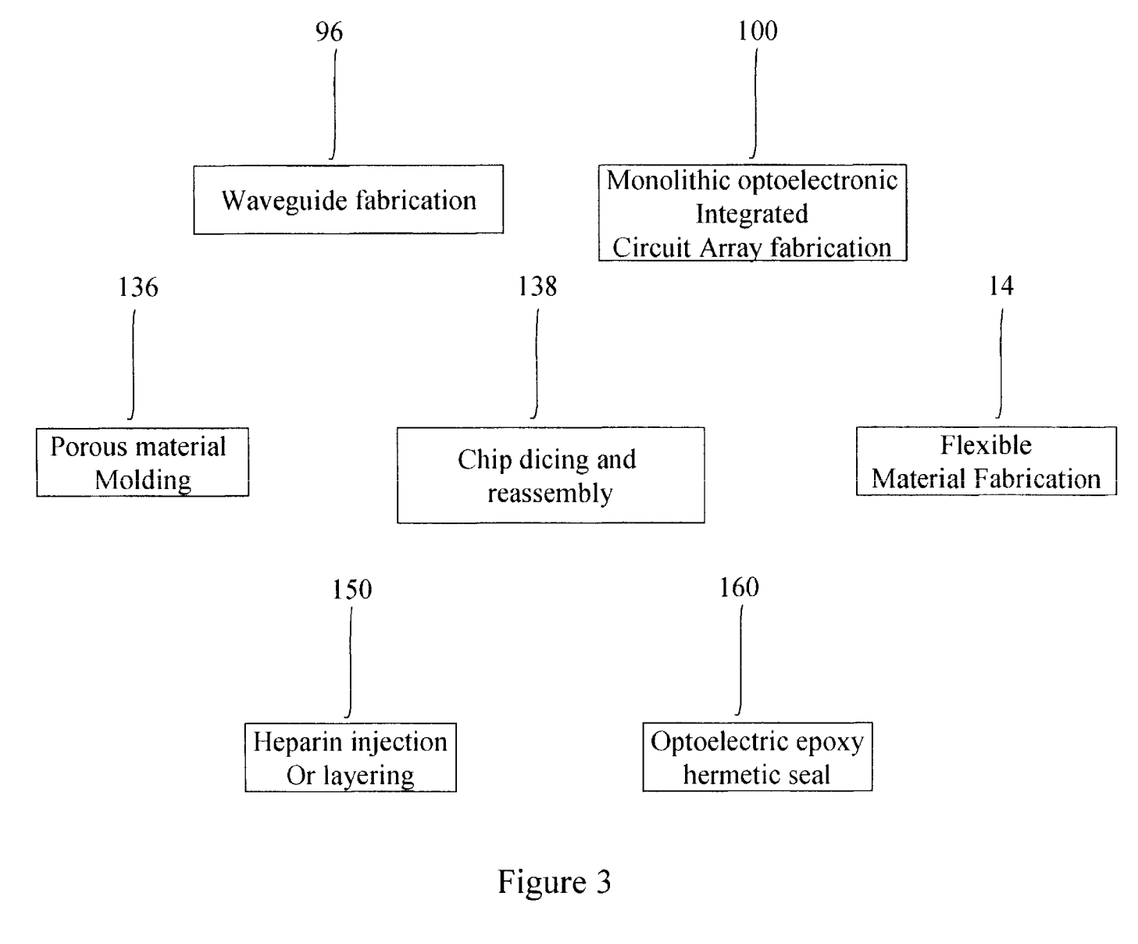
FIG. 3 is a flow diagram illustrating one preferred process for producing the particle analyzer of FIG. 1.
Figure 4A:
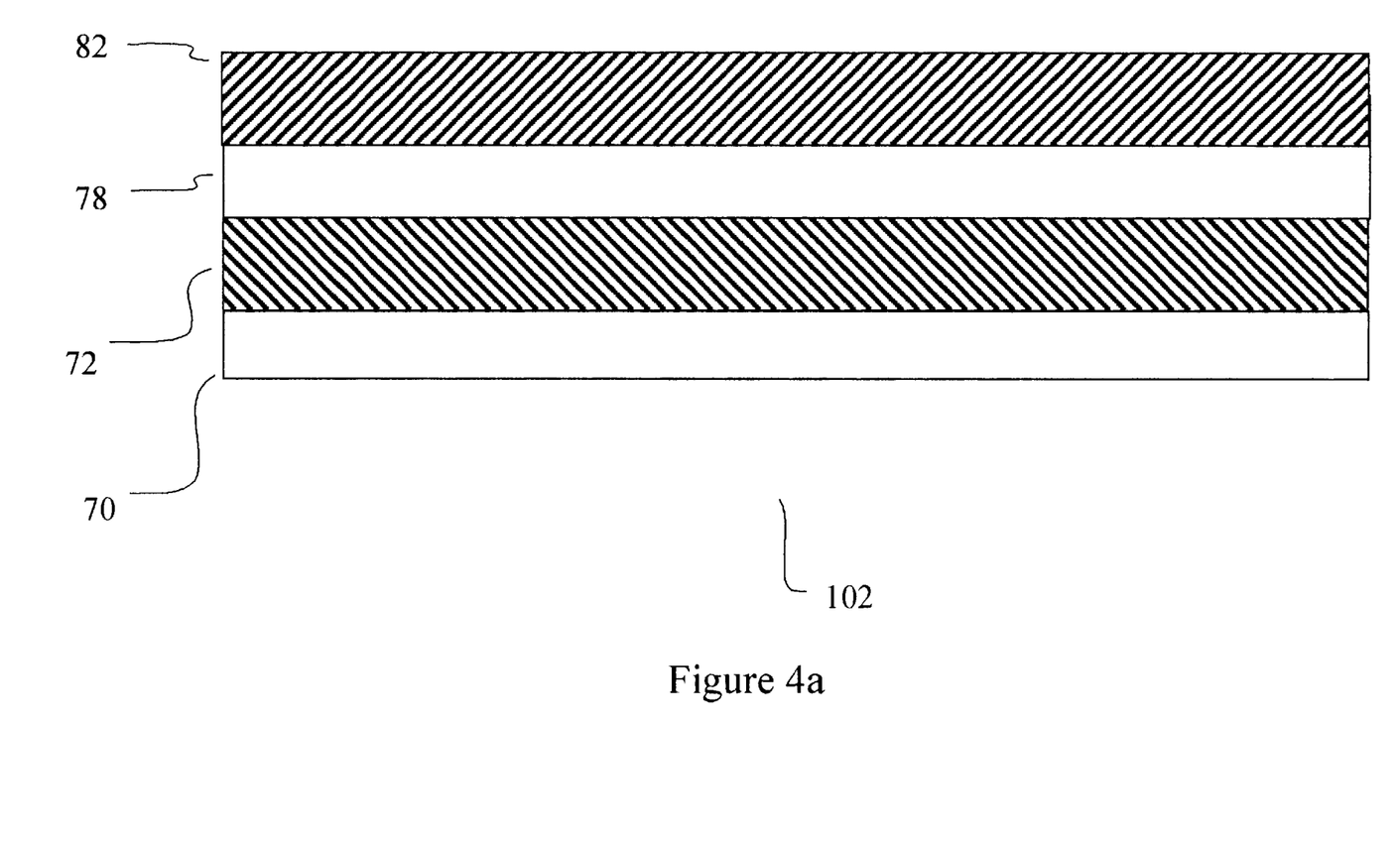
FIG. 4a is a schematic of one preferred epitaxial structure during fabrication of one preferred monolithic integrated circuit chip that is used in the assembly of FIG. 1.

FIG. 3 is a flowchart illustrating one preferred fabrication process of the instant invention. Referring to FIG. 3, and in the preferred embodiment depicted therein, in step 100 an integrated optoelectronic integrated circuit is fabricated onto a substrate. One preferred embodiment 102 for an epitaxial structure to eventually become the integrated circuit 100 is illustrated in FIG. 4*a*. The embodiment depicted in FIG. 4*a* may be produced in substantial accordance with the procedure described in U.S. Pat. No. 6,148,016 ("Integrated semiconductor lasers and photodetectors"), the entire disclosure of which is hereby incorporated by reference into this specification. This patent discloses and claims a method for fabricating a vertical cavity laser adjacent to a vertical cavity photodetector, through the fabrication of an epitaxial structure comprising a substrate, a first mirror, a second mirror, and an emission/absorption cavity between said first and second mirrors.

Figure 4B:
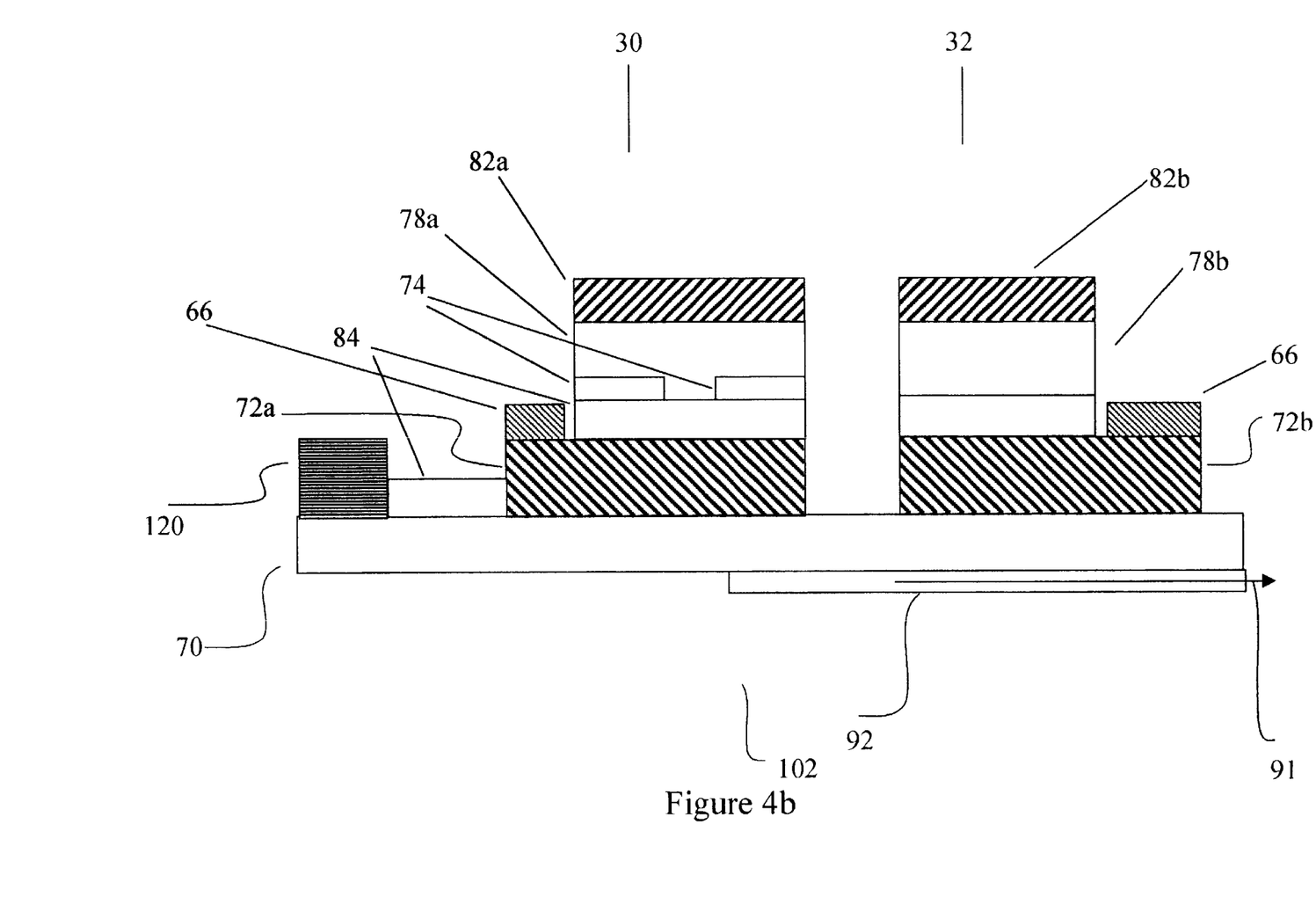
FIG. 4b is a schematic of one preferred monolithic integrated circuit chip which is used in the assembly of FIG. 1.

In the embodiment depicted in FIGS. 4A and 4B, unnecessary and/or conventional detail has been omitted for the sake of simplicity of representation.

As will be apparent, and by means of further illustration, the device depicted in FIGS. 4*a* and 4*b* may be constructed by conventional means such as, e.g., the procedure disclosed in U.S. Pat. No. 6,097,748 ("Vertical cavity surface emitting laser semiconductor chip with integrated drivers and photodetectors and method of fabrication"), the entire disclosure of which is hereby incorporated by reference into this specification. This patent discloses and claims a vertical cavity surface emitting laser semiconductor chip comprising: (a) a vertical cavity surface emitting laser formed on a substrate; (b) a photodetector, integrated with the vertical cavity surface emitting laser for automatic power control of the vertical cavity surface emitting laser; and (c) a laterally integrated driver circuit, formed on the substrate, and about a periphery of the substrate, the driver circuit characterized as receiving feedback from the photodetector and adjusting an output power of the vertical cavity surface emitting laser in response to the feedback. Each of these elements is present in applicants' device.

Referring again to FIG. 4*a*, and in the preferred embodiment depicted, substrate 70 preferably consists essentially of ceramic semiconductor material such as, e.g., such as gallium arsenide, silicon, sapphire, mixtures thereof, and the like. Other suitable semiconductor materials will be apparent to those skilled in the art.

The device of this invention comprises an integrated vertical cavity laser/photodetector 24. As is known to those skilled in the art, the vertical cavity laser comprises a substrate, a bottom mirror, a top mirror and a cavity with a gain medium between the top and bottom mirrors. The gain medium typically comprises quantum wells which, when electrically or optically pumped, will emit light. The mirrors typically comprise distributed bragg reflectors (DBRs) formed from alternating high/low index quarter-wave thick layers. Multilayer stacks are generally used for the mirrors instead of metal due to the high reflectivity (>99%) needed to achieve lasing because the gain medium is so thin. Bottom-emitting or top-emitting VCSELs have a partially transmissive bottom or top mirror, respectively. Because of the highly reflectivity mirrors and short cavity used in VCSELs, the lasing wavelength is controlled by the resonant wavelength of the cavity, rather than the peak of the gain as in in-plane lasers.

Referring again to FIG. 4*a*, disposed on substrate 70 is a distributed multi-layered bottom bragg reflector (DBR) 72; and, deposited onto the DBR 72 is an emission/absorption cavity 78. Thereafter, a second, multilayered top DBR 82 is deposited onto the emission/absorption cavity 78.

The multi-layered bottom and top DBRs 72 and 82, as well as emission/absorption cavity 78 generally are preferably made of layers of aluminum gallium arsenide. These layers of the bottom and top DBRs 72 and 82 are fabricated so that an aluminum concentrations of these layers vary alternately in concentration. The reflectivity of a particular layer is a function of, e.g., its aluminum concentration. It is preferred that the bottom DBR layer 72 have a lower aluminum concentration than the top DBR layer 82.

Additionally, the bottom and top DBRs 72 and 82 are preferably alternately doped with either a p-type dopant or an n-type dopant. For example, the top DBR 82 can be doped with the n-type dopant, whereas the bottom DBR 72 can be doped with the p-type dopant.

Emission/absorption cavity 78 is also made of a variety of layers. Emission/absorption cavity 78 is typically made of a quantum well with barrier regions on either side of the quantum well using any suitable materials. Generally, the barrier regions and the quantum well are made of undoped aluminum gallium arsenide, and gallium arsenide, respectively, each having a thickness of approximately 100 Angstroms. It should be understood by one of ordinary skill in the art that additional barrier layers and quantum wells can be added to improve performance of the emission/absorption cavity 78.

Referring to both FIGS. 4*a* and 4*b*, the bottom and top DBRs 72 and 82, emission/absorption cavity 78, and contacts 66 may be disposed or grown on substrate 70 by any suitable epitaxial method or technique, such as "Metal Organic Chemical Vapor Deposition" (MOCVD), "Molecular Beam Epitaxy" (MBE), "Chemical Beam Epitaxy" (CBE), or the like.

Referring again to FIG. 4*a*, the DBR/cavity/DBR layers of the VCSEL 32 and photodetector 30 are separated using conventional etching.

Most VCSELs are "top emitting" devices, that is, light is emitted outward or away from the top surface of the device. However, bottom-emitting devices, where light is emitted through the substrate, are advantageous for systems with arrays of vertical cavity lasers, because the driver circuitry can then be "flip-chip bonded" to the array instead of making individual wire bonds.

Referring again to FIG. 4*b*, the placement of the driver circuitry 120 on the substrate 70 is depicted. Reference to such driver circuitry can be found in U.S. Pat. No. 6,097,748 ("Vertical cavity surface emitting laser semiconductor chip with integrated drivers and photodetectors and method of fabrication"), the entire disclosure of which is hereby incorporated by reference into this specification.

Disposed on substrate 70 are air/oxide isolators, 74 which isolate electromagnetic radiation and prevent spurious radiation leakage out of the emission cavity region 78*a* within the VCSEL. As is known to those skilled in the art, these air/oxide isolators are often made of any suitable dielectric material, such as silicon dioxide ($SiO_2$), silicon nitride ($Si_3N_4$), or the like.

Referring again to FIG. 4*b*, the conductive layer 84 and contacts 66 are preferably made of any suitable conductive material, such as a metal (e.g., gold, silver, copper, aluminum, tungsten, an alloy (e.g., aluminum/copper (Al/Cu), titanium tungsten (TiW)), or the like. Deposition of the conductive layer 84 and the contacts 66 can be achieved by conventional means such as, e.g., sputtering, evaporation, and the like.

The specific thickness of conductive layer 84 will change with specific applications and designs. Such thickness of conductive layer 84 can range from 2,000 to 10,000 Angstroms, with a preferred range from about 3,000 to about 8,000 Angstroms, and having a nominal thickness of 4,000 Angstroms.

As is apparent, a masking layer can be patterned to make openings that expose portions of the surface to be masked. The masking layer can be made by any suitable lithographic process, such as photolithography, X-ray lithography, or the like. Generally, lithographic processes are well known in the art; however, by way of example, a brief explanation of a positive photolithographic process is provide herein below.

In such a process, a photolithographic material, such as photoresist, or the like, is applied to a surface. The photolithographic material is exposed with a pattern of light and developed, thereby providing open areas as well as covered areas. The pattern that is used to expose the photolithographic material can form any number of geometric patterns and designs, such as rings, ovals, lines, squares, or the like.

After the exposing and developing processes of the masking layer, the substrate or surface is ready to be etched. The surface of substrate 70 is etched in any suitable etch system that provides an anisotropic etch profile. Further, any suitable etch chemistry is used for etching substrate 70/surface, such as a fluorine based chemistry, a chlorine based chemistry, or the like. Generally, fluorine based chemistry is used to etch or remove a variety of materials, such as nitride, silicon dioxide, tungsten, titanium tungsten, and the like; whereas the chlorine based chemistry also is used to remove a variety of material, such as semiconductor materials, e.g., silicon, gallium arsenide, aluminum gallium arsenide, as well as conductive materials, such as aluminum, e.g., copper, aluminum, and the like. Additionally, it should be understood that these chemistries can be used in the same etching system, thereby enabling a multitude of layers or different materials to be etched in one etching system. Thus, the process of manufacturing a vertical cavity surface emitting laser is more manufacturable.

Referring again to FIG. 4*b*, an optical waveguide 92 is contiguous with porous layer 134 (see FIG. 8 for more detail) and is adapted to transmit light in directions of arrow 91. It is preferred that the waveguide 92 be fabricated of glass and that the substrate be silicon. See U.S. Pat. No. 6,167,168.

In one preferred embodiment, waveguide layer 92 has a geometry adapted to transmit visible light at a high efficiency. Reference may be had to, e.g. U.S. Pat. No. 6,167,168 ("Arrangement of optical waveguides"), the entire disclosure of each of which is hereby incorporated by reference into this specification. The waveguide(s) 92 may be coupled, one to another, or to photodetector 32, by conventional waveguide coupling means. See, e.g., U.S. Pat. No. 5,805,751 ("Wavelength selective optical couplers"). The entire description of each of these United States patents is hereby incorporated by reference into this specification.

In one embodiment, depicted in FIG. 4*b*, the waveguide array 92 is positioned under only the photodetector 32 region and is not so positioned under VCSEL 30.

In one embodiment, not shown, the device 102 comprises at least two optical waveguides 92 of which each comprises an input-side end for coupling an optical waveguide into the waveguides, a respective output-side end for coupling out the optical waveguides conducted in the waveguide, and a determined optical length between the two ends. In one aspect of this embodiment, the device 102 contains first means for producing a modification of the optical length of the waveguide so that in a waveguide, the produced modification of the optical length is smaller than in another waveguide.

In one embodiment, not shown, the waveguides are arranged next to one another at a spatial distance small enough that the optical waves coupled out from these ends are superposed coherently on one another and that at least two of the waveguides are dimensioned so that their optical length is different from one another and that the optical length is modified to increase from wavelength to wavelength. Preferably, two means are provided, with the first means causing different amounts of increase of wavelength in one direction, while the second means causes decreasing amounts of change in wavelength the one direction. In one embodiment, not shown, there is utilized a phased array with several optical waveguides with optical lengths that increase from waveguide to waveguide. This phased array has a first arrangement for modifying the optical length of waveguides, with the modification increasing from waveguide to waveguide in one direction, and a second arrangement for producing a modification of the optical length, with the modification decreasing from waveguide to waveguide in the one direction.

The aforementioned discussion regarding waveguides is known to those skilled in the art. Thus, for example, in U.S. Pat. No. 6,091,874 ("Flexible optical waveguide device and process for the production thereof") there is disclosed a flexible optical waveguide device obtained by forming a refractive index distribution in a light-permeable polymer film to obtain an optical wave-guide film and forming a cured resin layer on at least one surface of the optical wave-guide film, the cured resin layer(s) comprising, as main components, a polyamide resin, and at least one member selected from the group consisting of an epoxy resin and a phenolic resin; and the flexible waveguide used in applicants' device may be made in accordance with the process of such patent. The entire disclosure of which is hereby incorporated by reference into this specification.

In one embodiment, when fabrication of the optoelectronic devices and waveguides is completed the individual optoelectronic devices 24 is be diced in the manner known to those skilled in the art.

The devices 24 are then assembled into forming array 126/128/130/132. Each individual device 24 may be coupled to a flexible waveguide and linked by any suitable means (via, e.g., link 140) to the next device.

At temperatures required for the fabrication of the optoelectronic device 24 and the waveguide array 92, the stent portion of the device may be fabricated separately. In one preferred embodiment, the stent can be initially constructed as a flat layered sheet where a flexible biocompatible layer 12 will then be coated with a solution of heparin and water. The outer edges of the sheet 12 can be seamed for when the device is formed into a cylinder. With regard to the application of heparin, and/or other anticoagulant, the heparin may be applied to the surface simply from aqueous solution or dispersion. For example, heparin can be applied from aqueous solution onto a stent body and allowed to dry. A heparin/water solution may be applied to the stent body in successive thin coats with drying and weighing of the stent between coats. When the total weight of coating on the stent indicates that the target dosage has been achieved, no additional heparin solution is applied. The overall coating should be thin enough so that it will not significantly increase the profile of the stent for intravascular delivery by catheter. It is therefore preferably less than about 0.002 inch thick and most preferably less than 0.001 inch thick. The porous polymeric overlayer can then be applied to the heparin coated stent body such that it controls the release of heparin from the coating.

Figure 5:
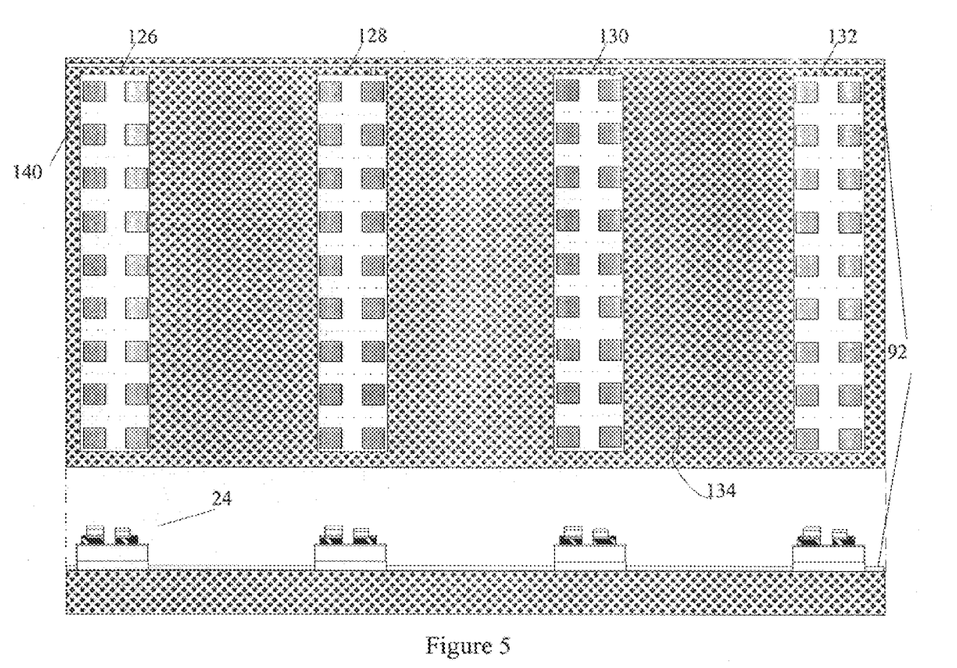
FIG. 5 is a schematic of a multiplicity of the monolithic integrated circuit chips of FIG. 4b disposed on a porous substrate and waveguide array.

FIG. 5 is a partial view of the interior surface 26 of device 10 (see FIG. 1), showing it in a flat configuration to better illustrate its components. Referring to FIG. 5, it will be seen that optoelectronic circuit arrays 126, 128, 130, and 132 are bonded to porous material 134. This bonding may be affected by conventional means such as, e.g., by the use of epoxy adhesive. Thus, e.g., one may use as an adhesive Emerson & Cuming Stycase® 1267 or 1269 transparent, high-impact casting resins or Epoxy Technology, Inc. Epotek® 301; these are spectrally transparent epoxies which have appropriate transmissions between 900 and 350 nanometers.

The structure depicted in FIG. 5 has several features in common with the structure claimed and disclosed in U.S. Pat. No. 5,865,814 ("Blood contacting medical device and method") the entire disclosure of which is hereby incorporated by reference into this specification. This patent claims a medical device for use in contact with circulating blood comprising: (a) a medical device having a blood-contacting surface; (b) a first coating layer on the blood-contacting surface consisting essentially of water soluble heparin; and (c) a second coating layer comprising a porous polymer overlaying the first coating layer such that heparin is elutable from the medical device through the second coating layer.

The porous layer 134 may be similar to or identical to the porous layer described in such patent. Thus,. e.g., it may be comprised of a polymer selected from the group consisting of poly(lactic acid), poly(lactide-co-glycolide) and poly (hydroxybutyrate-co-valerate), and mixtures thereof. Thus, e.g., it may be comprised of a polymer selected from the group consisting of silicones, polyurethanes, polyesters, vinyl homopolymers and copolymers, acrylate homopolymers and copolymers, polyethers and cellulosics. Thus, e.g., it may have an average pore diameter in the range of about 0.5–10 microns.

The porous layer 134 may, but need not, comprise materials such as biomolecules, including, e.g., fibrin, fibrinogen, cellulose, starch, collagen and hyaluronic acid. Also, biostable polymers with a relatively low chronic tissue response such as polyurethanes, silicones, and polyesters could be used, and other polymers could also be used if they can be dissolved and cured or polymerized on the stent. Such polymers include, e.g., polyolefins, polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefms, such as ethylenemethyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayontriacetate; cellulose, cellulose acetate, cellulose butyrate; cellulose acetate butyrate; cellophane; cellulose nitrate; cellulose propionate; cellulose ethers; and carboxymethyl cellulose.

A suitable porous coating can be provided, for example, by phase inversion precipitation of the polymer in the overlayer. According to this technique, a solution of a polymer is prepared in a mixture of two miscible solvents, one of which being a poorer solvent for this polymer and less volatile than the other solvent. When the solution is allowed to dry, there becomes a moment when the good solvent has sufficiently evaporated for causing the polymer to slowly precipitate which results, after complete drying, in an opened porous structure. For example, when using poly(L-flactic acid) as the polymer, a suitable solvent composition can include about a 40/60% (w/w) isooctane/chloroform solution. This solution should be mixed carefully to avoid precipitation during the mixing process. The better solvent for the polymer should dissolve the polymer first (i.e. a solution of poly(L-lactic acid) and chloroform should be made first). A mixture of the solvents should then be added to the polymer solution to bring the ingredients to the desired concentration (i.e. a mixture of isooctane and chloroform is added to the poly[L-lactic acid] solution). This mixture is then applied to the stent in the same manner as set forth above. It will be appreciated by those skilled in the art that the nature of the ingredients and the relative concentrations of the ingredients will determine the size of pores. Pores in the range of about 0.5 to 10 microns in diameter may be suitable. Phase inversion precipitation techniques are well known in the manufacture of porous polymeric membranes.

Figure 6:
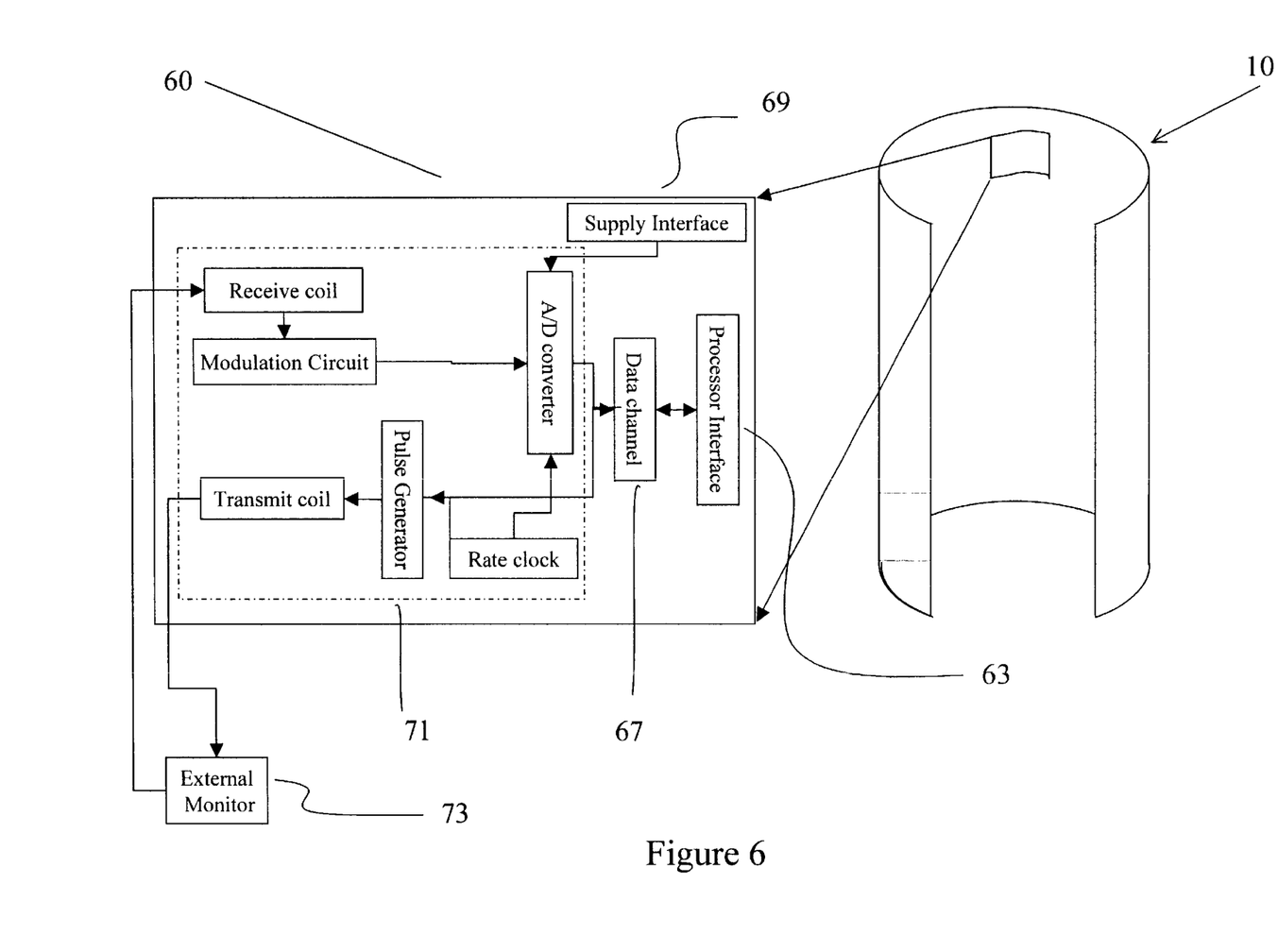
FIG. 6 is a partial exploded view of the particle analyzer of FIG. 1 illustrating a preferred telemetric device used therein.

FIG. 6 is a schematic of a preferred embodiment of a telemetry device 60 which, in the embodiment depicted, is affixed to the inner surface 26 of the device 10. In another embodiment, not shown, the telemetry device 60 is sealed within the outer casing 12 of device 10, near the exterior surface of such device 10.

Referring to FIG. 6, and in the preferred embodiment depicted therein, telemetry device 60 is in the form of an electronic circuit module which has a substantially rectangular cross-sectional shape. In one embodiment, the module 60 has a thickness of from about 0.01 to about 0.05 inches.

In the embodiment depicted, module 60 is comprised of a means for transmitting data from the telemetry interface 65 of processing/controlling device 64 (see FIG. 7) to the processor interface 63 of telemetry module 60. In the embodiment depicted, input and output data are coordinated through a data channel 67.

A power supply interface 69 transfers power from supply 61 (see FIG. 7) to one or more of the active devices within module 60.

Referring again to FIG. 6, it will be seen that various active devices are enclosed within the dotted line structure 71. It will be apparent to those skilled in the art how each such device functions and is powered.

By way of illustration and not limitation, one may use the device disclosed in U.S. Pat. No. 5,683,432 ("Adaptive, performance-optimizing communication system for communicating with an implanted medical device".). This patent claims a system comprising an implantable medical device and an associated device, each provided with a transmitter/receiver, wherein the system is further provided with means for optimizing communication between said implanted device and said associated device, said optimizing means comprising: means associated with said transmitter/receivers for defining a plurality of telemetry transmission types and for defining in conjunction with each of said telemetry types a prioritized set of a plurality of performance goals which vary depending upon telemetry transmission type; means associated with said transmitter/receivers for controllably altering a plurality of operational parameters of said transmitter/receivers; means associated with said transmitter/receivers for determining whether a transmission between said transmitter/receivers meets said performance goals; and means associated with said transmitter/receivers for selecting among said operational parameters and adjusting said selected operational parameters based upon said prioritized set of performance goals to achieve said performance goals in order of their priority. The entire disclosure of this United States patent is hereby incorporated by reference into this specification.

By way of further illustration, one may use the telemetry system disclosed in U.S. Pat. No. 5,342,408 "Telemetry system for an implantable cardiac device"), the entire disclosure of which is herby incorporated by reference into this specification. This patent claims a device in which ". . . said circuit means including data generating means for generating data indicative of said monitored activity or therapeutic activity in accordance with received command transmissions; and telemetry means for communicating with a non-implanted external receiver and transmitter, said telemetry means including receiving means for receiving said command transmissions from said non-implanted external transmitter, said command transmissions conforming to a first protocol and said command transmissions being selectively transmitted at two or more rates in accordance with said first protocol; and transmitting means for transmitting information including said data to said non-implanted external receiver in accordance with a second protocol, said information transmissions being selectively transmitted at one or more rates in accordance with said second protocol, said first protocol being different from said second protocol. The entire disclosure of this United States patent is hereby incorporated by reference into this specification.

By way of further illustration, one may use the telemetry receiver disclosed in U.S. Pat. No. 5,466,246 ("Telemetry receiver for implantable device, incorporating digital signal processing"), the entire disclosure of which is hereby incorporated by reference into this specification. This patent claims an "apparatus for receiving a modulated data signal transmitted from an implantable device, wherein the modulated data signal is modulated by a digital or an analog data signal in any of a plurality of distinct modulation modes, the apparatus comprising: front-end receiving means for receiving the modulated data signal from the implantable device, the front-end receiving means including means for amplifying and antialias filtering the received signal; analog-to-digital converter means for sampling the amplified modulated data signal to produce a sequence of digitized samples; and digital signal processing means for filtering the sequence of digitized samples using at least one of a plurality of bandpass filters and for demodulating the filtered sequence of digitized samples using at least one of a plurality of demodulators, including an amplitude demodulator, a frequency demodulator, and a phase demodulator, to produce a demodulated data signal.

Referring again to FIG. 6, the a signal from the transmit coil of telemetry device 60 is received by an external monitoring device 73. One may use any of the external monitoring devices known to those skilled in the art. Thus, by way of illustration and not limitation, one may use system disclosed in U.S. Pat. No. 6,167,312 ("Telemetry system for implantable medical devices"), the entire disclosure of which is hereby incorporated by reference into this specification. This patent claims: "An external device for use in communication with an implantable medical device, comprising: a device housing, a device controller, mounted within the device housing; a spatial diversity antenna array mounted to the device housing, an RF transceiver operating at defined frequency, located within the device housing, coupled to the antenna array; means for encoding signals to be transmitted to the implantable device, coupled to an input of the transceiver; means for decoding signals received from the implantable device, coupled to an output of the transceiver; and means for displaying demodulated signal received from the implanted device, mounted to the device housing, wherein the antenna array comprises a first antenna permanently mounted to the device housing and a second antenna removably mounted to the device housing and locatable at a distance from the housing and means for coupling the removable antenna to the RF transceiver while the removable antenna is located at a distance from the device housing, and wherein the device controller includes means for selecting which of the two antennas in the antenna array is coupled to the transceiver.

Other external receiving/monitoring means may also be used.

FIG. 7 is a schematic of a device 64 for communicating with the photodetector/laser array 126, 128, 130, and 132 (see FIG. 5). Referring to FIG. 7, the device 64, in the embodiment depicted, is affixed to the inner surface 26 of the device 10. In another embodiment, not shown, the device 64 is sealed within the outer casing 12 of device 10, near the exterior surface of such device 10.

Referring to FIG. 7, and in the preferred embodiment depicted therein, device 64 is in the form of an electronic circuit module which has a substantially rectangular cross-sectional shape. In one embodiment, the module 64 has a thickness of from about 0.01 to about 0.05 inches.

In the embodiment depicted in FIG. 7, various active devices are illustrated within dotted line 75. As will be apparent to those skilled in the art, other combinations of active devices also may be used. Regardless of the particular combination used, the module 64 contains means for receiving optical signals (see, e.g., waveguide interface 77), means for signaling to optical drivers 120 (see, e.g., VSCEL Control Interface 79), means for converting one or more optical signals into one or more electrical signals (see, e.g., Optical Electronic conversion device 81), means for integrating electronic signals in a parallel fashion through a parallel interface (see, e.g., Parallel Interface 83), and means for controlling one or more lasers and for integrating various signals from the photodectors (see, e.g., microprocessor 85).

Figure 8:
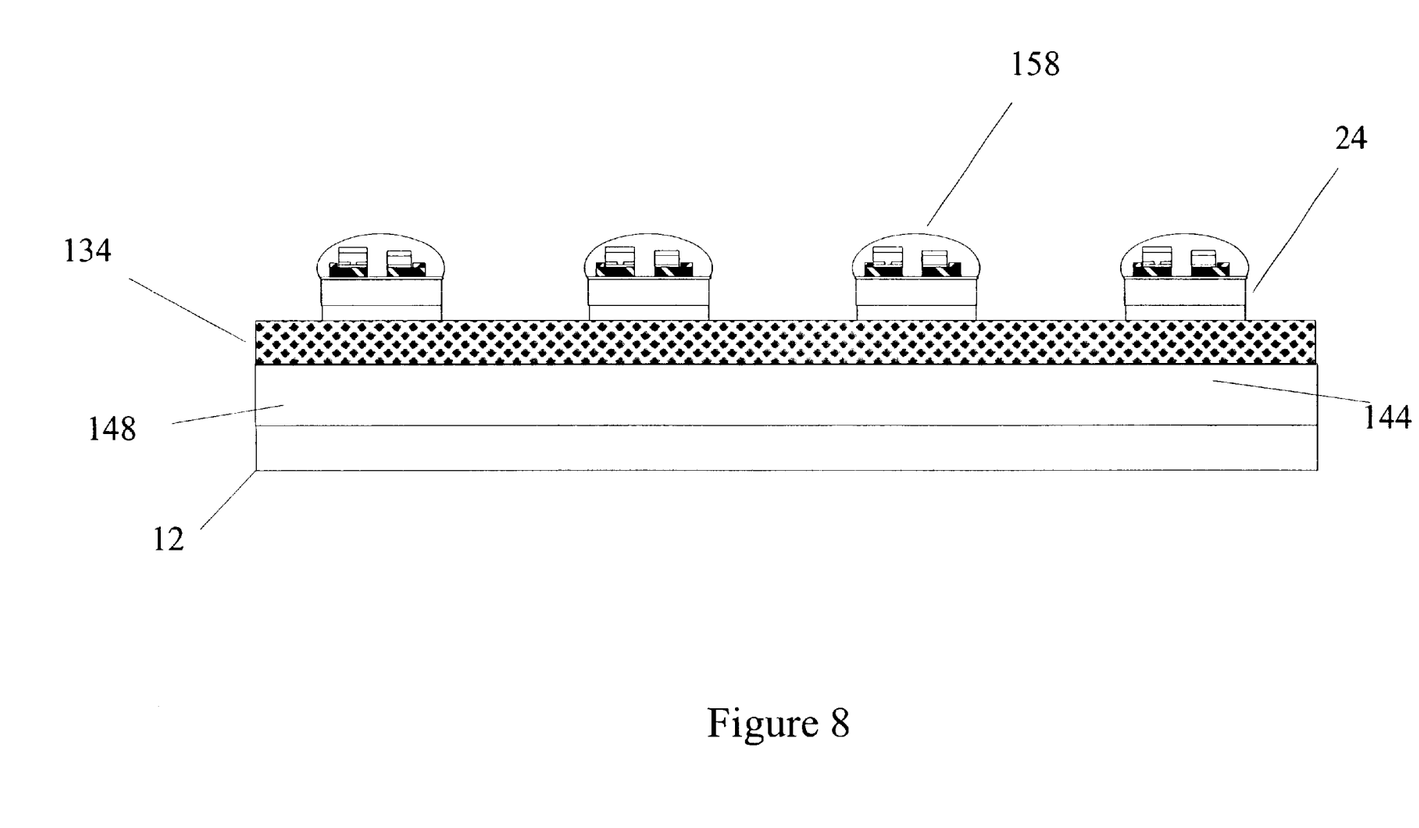
FIG. 8 is a schematic diagram of one preferred body of the particle analyzer, which comprises an opaque covering on a portion of the inner surface of the analyzer with additional underlying layers depicted.

Referring to FIG. 8, and in the preferred embodiment depicted therein, it will be seen that a transparent seal 158 is disposed over each optical electronic device 24. One may use transparent sealing means known in the art. Thus, e.g., some of the materials which may be used, and means for using them to seal a device, are described in U.S. Pat. No. 5,556,421 ("implantable medical device with enclosed physiological parameter sensors or telemetry link"), the entire disclosure of which is hereby incorporated by reference into this specification.

In the embodiment depicted in FIG. 8, the thickness of the transparent layer 158 is increased for illustration purposes only and layers are not drawn to scale. The actual thickness of the transparent layer 158 preferably has a transmissivity for electromagnetic energy as required by the particular sensor or communication mechanism employed in the implantable device 10 (see FIG. 1). The transparent layer 158 preferably is constructed of a suitable material that conducts electromagnetic energy without excessive absorption or reflection, thereby allowing the embedded VCSEL/ photodector arrays 126 et seq. to transmit and receive electromagnetic energy to and from a point external to the transparent layer 158. For many applications, the transparent layer 158 preferably is made of an epoxy resin or similar thermosetting polymer material which is formed in situ In addition to epoxy, other material suitable for layer 158 include glass, plastics and elastomers (such as Dow Chemical's Pellethane) and ceramic materials (such as sapphire).

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

We claim:

1. An implantable stent which comprises:
   (a) a tube comprising an inner surface and an outer surface, and
   (b) a multiplicity of optical radiation emitting means adapted to emit radiation with a wavelength from about 30 nanometers to about 30 millimeters, and a multiplicity of optical radiation detecting means adapted to detect radiation with a wavelength of from about 30 nanometers to about 30 millimeters, wherein said optical radiation emitting means and said optical radiation detecting means are disposed on the inside surface of said tube.

2. The implantable stent as recited in claim 1, wherein said implantable stent is comprised of a flexible casing with an inner surface and an outer surface.

3. The implantable stent as recited in claim 2, wherein said flexible casing is comprised of fluoropolymer.

4. The implantable stent as recited in claim 2, wherein said casing is optically impermeable.

5. The implantable stent as recited in claim 4, wherein a layer of anticoagulant material is disposed on said inner surface of said flexible casing.

6. The implantable stent as recited in claim 5, wherein said anticoagulant material is heparin.

7. The implantable stent as recited in claim 5, wherein a layer of porous material is disposed and top of said layer of anticoagulant material.

8. The implantable stent as recited in claim 7, wherein said layer of porous material has an average pore size of from about 0.5 to about 10 microns.

9. The implantable stent as recited in claim 8, wherein said layer of porous material is comprised of polymeric material.

10. The implantable stent as recited in claim 1, wherein said implantable stent comprises telemetry means for transmitting a signal to a receiver located external to said implantable stent.

11. The implantable stent as recited in claim 10, wherein said implantable stent comprises telemetry means for receiving a signal from a transmitter located external to said implantable stent.

12. The implantable stent as recited in claim 11, wherein said signal transmitted by said implantable stent is a radio frequency signal.

13. The implantable stent as recited in claim 12, wherein said signal received by said implantable stent is a radio frequency signal.

14. The implantable stent as recited in claim 1, wherein said implantable stent is comprised of a waveguide array.

15. The implantable stent as recited in claim 14, wherein said waveguide array is comprised of a flexible optical waveguide device.

16. The implantable stent as recited in claim 15, wherein said waveguide array is comprised of means for transmitting optical energy in a specified configuration.

17. The implantable stent as recited in claim 16, wherein said implantable stent is comprised of a waveguide interface for receiving said optical energy transmitted in said specified configuration by said waveguide array.

18. The implantable stent as recited in claim 17, wherein said waveguide array is comprised of means for filtering specified optical frequencies.

19. The implantable stent as recited in claim 14, wherein said implantable stent is comprised of means for receiving optical energy from said waveguide array.

20. The implantable stent as recited in claim 19, further comprising means for processing said optical energy received from waveguide array.

21. The implantable stent as recited in claim 20, further comprising means for processing said radiation emitted by said optical radiation emitting means adapted with a wavelength from about 30 nanometers to about 30 millimeters.

22. The implantable stent as recited in claim 21, wherein said implantable stent comprises telemetry means for transmitting a signal to a receiver located external to said implantable stent.

23. The implantable stent as recited in claim 22, wherein said implantable stent comprises telemetry means for receiving a signal from a transmitter located external to said implantable stent.

24. The implantable stent as recited in claim 23, wherein said implantable stent is comprised of a controller operatively connected to said means for transmitting a signal to said receiver, and operatively connected to said means for receiving a signal from said transmitter.

25. The implantable stent as recited in claim 1, wherein a transparent seal is disposed over each of said optical radiation emitting means.

26. The implantable stent as recited in claim 25, wherein a transparent seal over each of said optical radiation emitting means.

27. The implantable stent as recited in claim 1, wherein said implantable stent is comprised of a multiplicity of vertical cavity surface emitting lasers and photodetectors arranged in a monolithic configuration.

28. The implantable stent as recited in claim 27, wherein said monolithic configuration further comprises a multiplicity of optical drivers operatively connected to said vertical cavity surface emitting lasers.

29. The implantable stent as recited in claim 27, wherein said vertical cavity surface emitting lasers each comprise a multiplicity of distributed Bragg reflector layers.

30. The implantable stent as recited in claim 29, wherein each of said photodetectors comprises a multiplicity of distributed Bragg reflector layers.

31. The implantable stent as recited in claim 30, wherein each of said vertical cavity surface emitting lasers is comprised of an emission layer disposed between a first distributed Bragg reflector layer and a second distributed Bragg reflector layer.

32. The implantable stent as recited in claim 31, wherein said emission layer is comprised of a multiplicity of quantum well structures.

33. The implantable stent as recited in claim 32, wherein each of said photodetectors is comprised of an absorption layer disposed between a first distributed Bragg reflector layer and a second distributed Bragg reflector layer.

34. The implantable stent as recited in claim 27, wherein each of said vertical cavity surface emitting lasers and photodetectors is disposed on a separate semiconductor substrate.

35. The implantable stent as recited in claim 34, wherein said semiconductor substrate comprises gallium arsenide.

36. The implantable stent as recited in claim 34, wherein said semiconductor substrate comprises silicon.

37. The implantable stent as recited in claim 1, wherein said implantable stent is comprised of an arithmetic unit.

38. The implantable stent as recited in claim 37, wherein said arithmetic unit is comprised of means for receiving signals from said optical radiation detecting means.

39. The implantable stent as recited in claim 38, wherein said arithmetic unit is comprised of means for calculating the concentration of components in an analyte disposed within said implantable stent.

40. The implantable stent as recited in claim 39, wherein said means for calculating the concentration of components in said analyte calculates concentrations of said components in said analyte based upon optimum optical path lengths for different wavelengths and values of transmitted light.

41. The implantable stent as recited in claim 1, wherein said implantable stent further comprises a power supply.

42. The implantable stent as recited in claim 41, wherein said power supply comprises a battery.

43. The implantable stent as recited in claim 42, wherein said battery is a lithium-iodine battery.

* * * * *